(12) United States Patent
Hilt

(10) Patent No.: US 8,357,382 B1
(45) Date of Patent: Jan. 22, 2013

(54) COSMETIC FORMULATIONS

(76) Inventor: Bethany L. Hilt, Cleveland, OH (US)

( * ) Notice: Subject to any disclaimer, the term of this patent is extended or adjusted under 35 U.S.C. 154(b) by 191 days.

(21) Appl. No.: 12/753,055

(22) Filed: Apr. 1, 2010

Related U.S. Application Data

(60) Provisional application No. 61/211,715, filed on Apr. 2, 2009.

(51) Int. Cl.
*A61K 8/00* (2006.01)
*A61K 8/02* (2006.01)
*A61K 8/18* (2006.01)
*A61Q 17/04* (2006.01)

(52) U.S. Cl. .......................................... 424/401; 424/59

(58) Field of Classification Search ........................ None
See application file for complete search history.

(56) References Cited

U.S. PATENT DOCUMENTS

| | | | | |
|---|---|---|---|---|
| 5,208,011 | A | * | 5/1993 | Vaughan .......................... 424/59 |
| 5,804,168 | A | * | 9/1998 | Murad ............................. 424/59 |
| 6,964,954 | B2 | * | 11/2005 | Dalko et al. ................... 514/178 |
| 2002/0159959 | A1 | * | 10/2002 | Borgnine ........................ 424/59 |
| 2006/0093634 | A1 | * | 5/2006 | Lutz et al. ...................... 424/401 |
| 2006/0198800 | A1 | * | 9/2006 | Dilallo et al. ................... 424/59 |
| 2006/0263399 | A1 | * | 11/2006 | Yasuno et al. ................. 424/401 |
| 2007/0065396 | A1 | * | 3/2007 | Morariu .......................... 424/74 |
| 2007/0154432 | A1 | * | 7/2007 | Davis ......................... 424/70.12 |
| 2007/0178061 | A1 | * | 8/2007 | Venturi et al. ................... 424/74 |
| 2010/0311667 | A1 | * | 12/2010 | Hocquaux et al. ........... 514/18.8 |

FOREIGN PATENT DOCUMENTS

| | | |
|---|---|---|
| WO | WO 2007117352 A2 * | 10/2007 |
| WO | WO 2009037061 A2 * | 3/2009 |

* cited by examiner

*Primary Examiner* — Juliet Switzer
*Assistant Examiner* — Caralynne Helm

(57) ABSTRACT

The invention relates to cosmetic formulations. In one embodiment, the present invention relates to cosmetic formulations for use on the skin (e.g., the skin of the face).

13 Claims, No Drawings

COSMETIC FORMULATIONS

RELATED APPLICATION DATA

This application claims priority to U.S. Provisional Patent Application No. 61/211,715 filed Apr. 2, 2009 and entitled "Cosmetic Formulations," the disclosure of which is hereby incorporated herein by reference in its entirety.

FIELD OF THE INVENTION

The invention relates to cosmetic formulations. In one embodiment, the present invention relates to cosmetic formulations for use on the skin (e.g., the skin of the face).

BACKGROUND OF THE INVENTION

A wide variety of cosmetic formulations are used every day. In most instances, they do not provide a sufficient number of compounds to address all of the needs of a daily skin regimen.

Given this, there is a need in the art for cosmetic formulations that are designed to provide to the skin a wide range of compounds, vitamins and/or other desirables.

SUMMARY OF THE INVENTION

The invention relates to cosmetic formulations. In one embodiment, the present invention relates to cosmetic formulations for use on the skin (e.g., the skin of the face).

In one embodiment, the present invention relates to a cosmetic formulation designed to provide to the skin a wide range of compounds, vitamins and/or other desirables. In another embodiment, the present invention relates to a cosmetic formulation as described herein.

In still another embodiment, the present invention relates to a cosmetic formulation comprising: (A) an alpha hydroxy acid; (B) a suitable form of vitamin A, a retinoid, a tazarotene, a tretinoin and/or a chemical compound chemically related to vitamin A; (C) one or more anitoxidants; (D) at least one UVA and/or UVB screening agent or a combination of at least one UVA screening agent in conjunction with at least one UVB screening agent; and (E) water.

In still yet another embodiment, the present invention relates to a cosmetic formulation comprising: (a) an alpha hydroxy acid; (b) a keratolytic salicylate or a form of willow bark extract; (c) a suitable form of vitamin A, a retinoid, a tazarotene, a tretinoin and/or a chemical compound chemically related to vitamin A; (d) an amino acid, a form of an amino acid, a protein or hydrolyzed rice bran protein, oxido reductases, *glycine soja* (soybean) protein; (e) one or more anitoxidants; (f) vitamin E or a form thereof; (g) at least one UVA and/or UVB screening agent or a combination of at least one UVA screening agent in conjunction with at least one UVB screening agent; (h) glycerin; (i) one or more polyacrylamide-based emulsifying agents; and (j) water.

In still yet another embodiment, the present invention relates to a cosmetic formulation comprising: (i) an alpha hydroxy acid; (ii) a keratolytic salicylate or a form of willow bark extract; (iii) a suitable form of vitamin A, a retinoid, a tazarotene, a tretinoin and/or a chemical compound chemically related to vitamin A; (iv) one or more of arbutin, a form of arbutin, a glycosylated benzoquinone, a glucosylated hydroquinone, a hydroquinone, kojic acid, a form of kojic acid, vitamin C, a form of vitamin C, niacinamide, a form of niacinamide, soy, a form of soy; a tyrosinase inhibitor, a form of a tyrosinase inhibitor, a melanin synthesis inhibitor, a form of a melanin synthesis inhibitor, and/or a plant extract of one or more portions of a bearberry, cranberry, blueberry, mushroom, pear, *mitracarpus scaber*, mulberry, lemon juice, *phyllanthus emblica*, daisy flower, *waltheria indica* and/or licorice; (v) an amino acid, a form of an amino acid, a protein or hydrolyzed rice bran protein, oxido reductases, *glycine soja* (soybean) protein; (vi) an omega-3, omega-6 and/or omega-9 fatty acid, or form thereof; (vii) one or more anitoxidants; (viii) vitamin E or a form thereof; (ix) at least one UVA and/or UVB screening agent or a combination of at least one UVA screening agent in conjunction with at least one UVB screening agent; (x) glycerin; (xi) a dermatologically acceptable form of silicone; (xii) one or more polyacrylamide-based emulsifying agents; (xiii) a pH buffering agent; and (xiv) water.

DETAILED DESCRIPTION OF THE INVENTION

The invention relates to cosmetic formulations. In one embodiment, the present invention relates to cosmetic formulations for use on the skin (e.g., the skin of the face).

In one embodiment, the present invention is a mixture of:
(i) an alpha hydroxy acid;
(ii) a keratolytic salicylate or a form of willow bark extract;
(iii) a suitable form of vitamin A, a retinoid, a tazarotene, a tretinoin and/or a chemical compound chemically related to vitamin A;
(iv) one or more of arbutin, a form of arbutin, a glycosylated benzoquinone, a glucosylated hydroquinone, a hydroquinone, kojic acid, a form of kojic acid, vitamin C, a form of vitamin C, niacinamide, a form of niacinamide, soy, a form of soy; a tyrosinase inhibitor, a form of a tyrosinase inhibitor, a melanin synthesis inhibitor, a form of a melanin synthesis inhibitor, and/or a plant extract of one or more portions (including where applicable the fruit thereof) of a bearberry, cranberry, blueberry, mushroom, pear, *mitracarpus scaber*, mulberry, lemon juice, *phyllanthus emblica*, daisy flower, *waltheria indica* and/or licorice;
(v) an amino acid, a form of an amino acid, a protein or hydrolyzed rice bran protein, oxido reductases, *glycine soja* (soybean) protein;
(vi) an omega-3, omega-6 and/or omega-9 fatty acid, or form thereof;
(vii) one or more anitoxidants;
(viii) vitamin E or a form thereof;
(ix) at least one UVA and/or UVB screening agent or a combination of at least one UVA screening agent in conjunction with at least one UVB screening agent;
(x) glycerin;
(xi) a dermatologically acceptable form of silicone (e.g., one or more of cyclopentasiloxane, cyclohexasiloxane, cyclomethicone, dimethicone, dimethicone copolyol, and/or dimethiconol);
(xii) one or more polyacrylamide-based emulsifying agents;
(xiii) a pH buffering agent (e.g., sodium hydroxide); and
(xiv) water.

Regarding component (i) of the above-mentioned cosmetic formulation the alpha hydroxy acid is in one embodiment selected from one or more of glycolic acid, lactic acid, malic acid, citric acid, tartaric acid, one or more other chemical compounds that consist of a carboxylic acid substituted with a hydroxy group on the adjacent carbon, a dicarboxylic acid, a polyhydroxy acid, or suitable mixtures of two or more thereof. In one embodiment, the amount of component (i) is in the range from about 5 percent by weight to about 25 percent by weight.

Regarding component (ii) of the above-mentioned cosmetic formulation, the amount of component (ii) is in the range from about 0.25 percent by weight to about 5 percent by weight. Regarding component (iii) of the above-mentioned cosmetic formulation, the amount of component (iii) is in the range from about 0.04 percent by weight to about 2 percent by weight. Regarding component (iv) of the above-mentioned cosmetic formulation, the amount of component (iv) is in the range from about 0.1 percent by weight to about 8 percent by weight. Regarding component (v) of the above-mentioned cosmetic formulation, the amount of component (v) is in the range from about 1 percent by weight to about 35 percent by weight.

Regarding component (vi) of the above-mentioned cosmetic formulation, the amount of component (vi) is in the range from about 0.1 percent by weight to about 10 percent by weight. Regarding component (vii) of the above-mentioned cosmetic formulation, the amount of component (vii) is in the range from about 0.01 percent by weight to about 8 percent by weight. Regarding component (viii) of the above-mentioned cosmetic formulation, the amount of component (viii) is in the range from about 0.01 percent by weight to about 8 percent by weight.

Regarding component (ix) of the above-mentioned cosmetic formulation the at least one UVA and/or UVB screening agent or the combination of at least one UVA screening agent in conjunction with at least one UVB screening agent comprises a suitable number of screening agents selected from titanium dioxide, zinc oxide, an ester of methoxycinnamic acid and 2-ethylhexanol, a benzophenone screening agent, an ester formed by the condensation of a salicylic acid with 2-ethylhexanol, or suitable combinations of two or more thereof. In one embodiment, the amount of component (ix) is in the range from about 2 percent by weight to about 25 percent by weight.

Regarding component (x) of the above-mentioned cosmetic formulation, the amount of component (x) is in the range from about 1 percent by weight to about 15 percent by weight. Regarding component (xi) of the above-mentioned cosmetic formulation, the amount of component (xi) is in the range from about 2 percent by weight to about 10 percent by weight. Regarding component (xii) of the above-mentioned cosmetic formulation, the amount of component (xii) is in the range from about 0.05 percent by weight to about 10 percent by weight. Regarding component (xiii) of the above-mentioned cosmetic formulation, the amount of component (xiii) is in the range from about 1 percent by weight to about 10 percent by weight.

In one embodiment, the cosmetic formulations of the present invention can be formulated to have any suitable pH. In one instance, the pH of the formulations of the present invention are between about 3.5 and about 9, between about 4 and about 8.5, between about 4.5 and about 8, between about 5 and about 7.5, between about 5.5 and about 7, or even between about 6 and about 6.5. In one instance, the formulations of the present invention are designed to be an exfoliant and therefore have a pH of less than about 4. Here, as well as elsewhere in the specification and claims, individual range limits, or values, can be combined to form additional non-disclosed ranges. In another embodiment, the cosmetic formulations of the present invention are designed to be skin care creams and can be designed to have any suitable pH level.

In still another embodiment, the present invention relates to a cosmetic formulation comprising: (A) an alpha hydroxy acid; (B) a suitable form of vitamin A, a retinoid, a tazarotene, a tretinoin and/or a chemical compound chemically related to vitamin A; (C) one or more anitoxidants; (D) at least one UVA and/or UVB screening agent or a combination of at least one UVA screening agent in conjunction with at least one UVB screening agent; and (E) water. The amounts of components (A) through (E) of this formulation can be selected from the ranges stated above for the similar components (i) through (xiv).

In still yet another embodiment, the present invention relates to a cosmetic formulation comprising: (a) an alpha hydroxy acid; (b) a keratolytic salicylate or a form of willow bark extract; (c) a suitable form of vitamin A, a retinoid, a tazarotene, a tretinoin and/or a chemical compound chemically related to vitamin A; (d) an amino acid, a form of an amino acid, a protein or hydrolyzed rice bran protein, oxido reductases, *glycine soja* (soybean) protein; (e) one or more anitoxidants; (f) vitamin E or a form thereof; (g) at least one UVA and/or UVB screening agent or a combination of at least one UVA screening agent in conjunction with at least one UVB screening agent; (h) glycerin; (i) one or more polyacrylamide-based emulsifying agents; and (j) water. The amounts of components (a) through (j) of this formulation can be selected from the ranges stated above for the similar components (i) through (xiv).

As would be apparent to one of skill in the art, the components of the present invention are selected in suitable amounts within the above stated ranges to yield a total of 100 weight percent. Given this, numerous combinations are within the scope of the present invention as any number of components can be varied within their stated ranges to achieve one or more desired cosmetic formulations.

EXAMPLE

The following is an illustrative example and the present invention is not limited thereto. Parts A, B, C, D and E are blended together in this example to yield a stable cosmetic formulation.

| Amount (grams) | Compound |
| --- | --- |
| Part A Amount | Part A Compound |
| 35.2% | Deionized Water |
| 5.0% | Glycerin (99.5% USP) |
| 0.5% | DL Panthenol |
| 0.25% | Allantoin |
| 0.25% | Formulex VTF-0873 (White Tea Extract) |
| 0.25% | Actiphyte of Blueberry |
| 0.05% | Bionatural Acai Extract |
| Part B Amount | Part B Compound |
| 7.5% | ESCALOL 557 (Octinoxate) |
| 5.0% | ESCALOL 587 (Octisalate) |
| 5.0% | ESCALOL 567 (Oxybenzone) |
| 5.0% | Montanov 68 |
| 2.5% | Neobee M-5 |
| 2.5% | Stearyl Alcohol |
| 1.0% | Grape Seed Oil |
| 1.0% | Borage Oil |
| 1.0% | Olive Oil |
| 1.0% | Jojoba Oil |
| 1.0% | Vitamin E Acetate |
| 1.0% | Salicylic Acid (USP) |
| 0.05% | Tinogard TT |
| Part C Amount | Part C Compound |
| 4.0% | Syn-Ake |
| 2.0% | Alpha Arbutin |

-continued

| Amount (grams) | Compound |
|---|---|
| 2.0% | Regu-Age |
| 1.0% | Sodium Hyaluronate—1% Solution |
| 0.2% | Aloe 200:1—Freeze Dried Powder |
| Part D Amount | Part D Compound |
| 10.0% | Purac PF 90—Lactic Acid |
| 0.75% | Suttocide A |
| 5.0% | Sodium Hydroxide (50% Solution) |
| Part E Amount | Part E Compound |
| 5.0% | WACKER CM 040 |
| 3.0% | WACKER CM 1000 |
| 2.0% | SEPIGEL 305 |
| 0.1% | Vitamin A Palmitate 1.7 With Tocopherol |
| 0.05% | Orange Oil Terpeneless |
| 0.01% | Lemongrass Oil |
| 100% | Total |

Although the invention has been described with reference to certain embodiments detailed herein, other embodiments can achieve the same or similar results. Variations and modifications of the invention will be obvious to those skilled in the art and the invention is intended to cover all such modifications and equivalents.

What is claimed is:

1. A cosmetic formulation comprising:
   (a) water;
   (b) glycerin;
   (c) a provitamin of vitamin B5;
   (d) allantoin;
   (e) a white tea extract;
   (f) a blueberry extract;
   (g) an acai extract;
   (h) at least one UVA and/or UVB screening agent;
   (i) stearyl alcohol;
   (j) grape seed oil;
   (k) borage oil;
   (l) olive oil;
   (m) jojoba oil;
   (n) vitamin E acetate;
   (o) salicylic acid;
   (p) an amino acid or a form of an amino acid;
   (q) an alpha arbutin;
   (r) hydrolyzed rice bran protein, oxido reductases, and/or *glycine soja* (soybean) protein;
   (s) sodium hyaluronate;
   (t) aloe or an extract from aloe;
   (u) lactic acid;
   (v) a dermatologically acceptable form of silicone;
   (w) one or more polyacrylamide-based emulsifying agents;
   (x) vitamin A palmitate;
   (y) orange oil; and
   (z) lemongrass oil.

2. The cosmetic composition of claim 1, wherein the amount of component (b) is in the range from about 1 percent by weight to about 15 percent by weight.

3. The cosmetic composition of claim 1, wherein component (h) comprises a screening agents selected from titanium dioxide, zinc oxide, an ester of methoxycinnamic acid and 2-ethylhexanol, a benzophenone screening agent, an ester formed by the condensation of a salicylic acid with 2-ethylhexanol, or combinations of two or more thereof.

4. The cosmetic composition of claim 1, wherein the amount of component (h) is in the range from about 2 percent by weight to about 25 percent by weight.

5. The cosmetic composition of claim 1, wherein the amount of component (n) is in the range from about 0.01 percent by weight to about 8 percent by weight.

6. The cosmetic composition of claim 1, wherein the amount of component (p) is in the range from about 1 percent by weight to about 35 percent by weight.

7. The cosmetic composition of claim 1, wherein the amount of component (o) is in the range from about 0.25 percent by weight to about 5 percent by weight.

8. The cosmetic composition of claim 1, wherein the amount of component (u) is in the range from about 5 percent by weight to about 25 percent by weight.

9. The cosmetic composition of claim 1, wherein the amount of component (v) is in the range from about 2 percent by weight to about 10 percent by weight.

10. The cosmetic composition of claim 1, wherein the amount of component (w) is in the range from about 0.05 percent by weight to about 10 percent by weight.

11. The cosmetic composition of claim 1, wherein the amount of component (x) is in the range from about 0.04 percent by weight to about 2 percent by weight.

12. The cosmetic composition of claim 1, wherein the pH of the composition is in the range of about 3.5 and about 9.

13. The cosmetic composition of claim 1, wherein the composition is an exfoliant and has a pH of less than about 4.

* * * * *